United States Patent
Andre et al.

(10) Patent No.: US 7,381,436 B2
(45) Date of Patent: Jun. 3, 2008

(54) **COSMETIC COMPOSITION IN PARTICULAR WITH ANTI-AGEING ACTIVITY COMPRISING AN EXTRACT OF *AFRAMOMUM ANGUSTIFOLIUM* OR *LONGOZA* PLANT**

(75) Inventors: Patrice Andre, Neuville aux Bois (FR); Isabelle Renimel, Trainore (FR); Nancy Sauvan, Orleans (FR); Hanitriniaina Razafimambimby, Fianarantsoa (MG)

(73) Assignee: LVMH Recherche, St. Jean-dé-Braye (FR)

( * ) Notice: Subject to any disclaimer, the term of this patent is extended or adjusted under 35 U.S.C. 154(b) by 0 days.

(21) Appl. No.: 11/543,561

(22) Filed: Oct. 4, 2006

(65) Prior Publication Data

US 2007/0122500 A1    May 31, 2007

(51) Int. Cl.
*A01N 65/00* (2006.01)
*A61K 36/906* (2006.01)

(52) U.S. Cl. .................................. 424/756
(58) Field of Classification Search ............ None
See application file for complete search history.

(56) References Cited

U.S. PATENT DOCUMENTS 5,879,682 A * 3/1999 Allas et al. ............ 424/756

OTHER PUBLICATIONS www.marketathome.com.*
www.sephora.com.*
Gaydou et al. "Etude de la composition en acides gras des huiles extraites de graines provenant de quelques plantes de Madagascar" Etudes et Recherches No. 4 p. 21-25 XP-009068392.
Baser et al. "The essential oils of *Aframomum corrorima* (Braun) Jansen and A.angustifolium K.Schum from Africa" Journal of Essential Oil Research v. 13(3): p. 208-209 (2001) abstract.
Githiori "Evaluation of Anthelmintic Properties of Ethnoveterinary Plant Preparations Used as Livestock Dewormers by Pastoralists and Small Holder Farmers in Kenya" Doctoral Thesis, Swedish University of Agricultural Sciences, Uppsala 2004, XP-002387646.
Hari et al. "The Volatile Fraction of *Aframomum sanguineum* (K. Schum) K. Schum. from Burundi" Journal of Essential Oil Research v. 6. p. 395-398 (Jul./Aug. 1994). XP-009068487.
Coomes et al. "*Aframomum angustifolium* seed from Zanzibar" Colonial Plant and Animal Products p. 68-77 (1955) XP-009098490.
Cousins "African Apes and Ethnomedicine" Gorilla Journal Dec. 25, 2002 XP-002387644.
Trabaud et al. "Madagascan *longoza* oil. Scented species of Hedychium" Chemical Abstracts Service, (1939) XP-002387849.
Rasoanaivo et al. "Essential Oils of Economic Value in Madagascar: Present State of Knowledge" HerbalGram. vol. 43, p. 31-39, 58-59 (1998) XP-002387645..

* cited by examiner

*Primary Examiner*—Christopher R. Tate
*Assistant Examiner*—Deborah A. Davis
(74) *Attorney, Agent, or Firm*—Merchant & Gould P.C.

(57) ABSTRACT

The present invention relates to a cosmetic composition.

This composition is characterized in that it comprises, as active ingredient, an extract of seeds of the *Aframomum angustifolium* or *Longoza* plant, optionally in a cosmetically acceptable excipient.

This cosmetic composition exhibits a good anti-ageing activity.

13 Claims, 2 Drawing Sheets

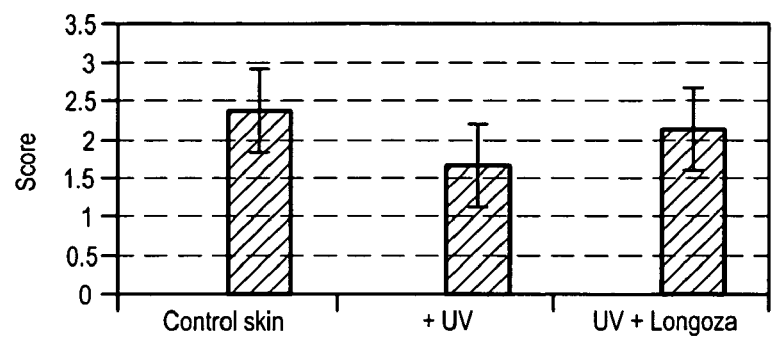
FIG.3
FIG.4B
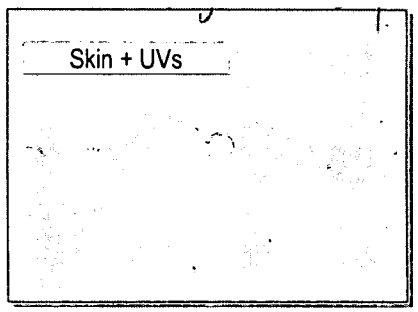
FIG.4A
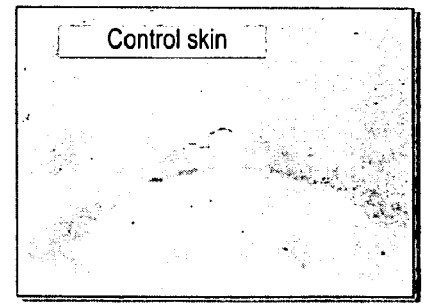
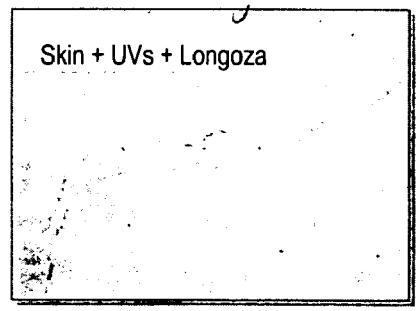
FIG.4C

COSMETIC COMPOSITION IN PARTICULAR WITH ANTI-AGEING ACTIVITY COMPRISING AN EXTRACT OF *AFRAMOMUM ANGUSTIFOLIUM* OR *LONGOZA* PLANT

The present invention relates essentially to a cosmetic composition, in particular with anti-ageing activity, characterized in that it comprises, as active ingredient, an extract of seeds of the *Aframomum angustifolium* or *Longoza* plant.

The invention also relates to the use of an extract of seeds of the *Aframomum angustifolium* or *Longoza* plant, as a cosmetic agent, especially for the production of a cosmetic composition, which in particular has an anti-ageing activity.

Hereinafter in the description and the claims, use will preferably be made, in the interest of simplification, of the term "*Longoza*", but this term obviously also signifies, without implied distinction, the *Aframomum angustifolium* plant.

PRIOR ART

The article by E. M. Gaydou et al., published in Revue française des Corps Gras [French review of fatty substances], No. 1 of January 1983, pages 21 to 25, describes a study regarding the fatty acid composition of oils extracted from seeds originating from some plants of Madagascar, including the *Aframomum angustifolium* plant (see Table 1, continuation 2, page 24). It is an extract of the seeds of the plant by means of an apolar solvent, in particular using hexane (see page 24, "Partie expérimentale" [Experimental section], 1st paragraph).

AIMS OF THE INVENTION

The aim of the invention is to solve the technical problem consisting of the provision of a solution for finding novel active ingredients as cosmetic agents which have a good anti-ageing activity, or an anti-ageing activity which is improved compared with the anti-ageing cosmetic agents previously known, and/or which have very good compatibility in the context of a topical application for cosmetic purposes, in particular to the skin, and/or which have no:, or substantially no, side or irritant effects.

The aim of the invention is to solve the technical problem stated above by means of an active ingredient obtained from a widely available or readily cultivatable natural source.

The aim of the invention is also to solve the technical problem stated above by also providing a method for obtaining the active ingredient which makes it possible to prepare sufficient amounts for use on an industrial scale, and in particular on a cosmetic scale.

SUMMARY OF THE INVENTION

The invention provides a solution to the technical problems stated above, in a simple, relatively inexpensive manner which can be used on an industrial scale, and in particular on a cosmetic scale.

According to a first aspect, the present invention provides a cosmetic composition, characterized in that it comprises, as active ingredient, an extract of seeds of the *Aframomum angustifolium* or *Longoza* plant, in a cosmetically acceptable excipient.

According to a second aspect, the invention also relates to the use of an extract of seeds of the *Aframomum angustifolium* or *Longoza* plant, as a cosmetic agent, for the production of a cosmetic composition.

According to an advantageous embodiment of the invention, the extract of *Longoza* is used as a cosmetic agent which has an anti-ageing activity.

According to an advantageous variant and implementation of the invention, the extract of seeds of the *Longoza* plant is used for an anti-wrinkle activity, in particular for decreasing, eliminating or slowing down the appearance of wrinkles, an action which preserves or restores the structure of the skin, especially by means of an action which stimulates the synthesis of collagen, in particular of collagen VII present at the dermal-epidermal junction or DEJ, and/or by means of an action on the oxytalan fibres and/or the elaunin fibres. Thus, the invention makes it possible to have an anti-wrinkling effect; an effect consisting of protection, repair or restoration of the elasticity and/or of the firmness of the skin. The invention also makes it possible to protect the skin against ageing resulting from the action of actinic radiation, in particular due to ultraviolet rays.

In the context of the invention, use will advantageously be made of an extract of the seeds of the *Aframomum angustifolium* or *Longoza* plant which has been prepared with an acceptable cosmetic solvent, in particular an alcoholic or aqueous-alcoholic solvent.

According to a specific embodiment of the invention, the plant-seed extract is obtained by means of a method of extraction comprising at least one step consisting of extraction of the ground seeds with an alcoholic or aqueous-alcoholic solvent.

Preferably, the grinding is carried out until a fine powder is obtained. The grains of this powder advantageously have a diameter of between approximately 0.01 and 1 mm.

According to an advantageous embodiment of the method according to the invention, an alcoholic or aqueous-alcoholic solvent in which the alcohol is a monoalcohol or a polyol containing from 1 to 4 carbon atoms, is used. Advantageously, this alcohol is chosen from methanol, ethanol, n-propanol, isopropanol, ethylene glycol, propylene glycol and butylene glycol, preferably ethanol. The extraction process can be carried out either at ambient temperature or at a temperature which can range up to boiling point of the solvent at atmospheric pressure, or even under a higher pressure such that, however, the boiling point does not exceed approximately 120° C. The relative proportion between the alcohol and the water is preferably chosen within a range of from 30/70 to 100/0 by volume.

Several successive extractions can be carried out until the material to be extracted has been completely depleted by the solvent under consideration.

The extraction time varies according to the solvent under consideration, the temperature and, optionally, the pressure used, so as to result in total depletion of the extracting material. In practice, this time will be limited to less than half hour for a profitable industrial exploitation. It will generally be of the order of 30 minutes.

According to a specific variant of implementation of this extraction method, the alcoholic or aqueous-alcoholic extract obtained is advantageously defatted by elimination of the lipids by means of at least one step consisting of extraction with an apolar organic solvent, for example hexane or n-heptane, thus obtaining a defatted alcoholic or aqueous-alcoholic extract.

According to a specific embodiment of this extraction method, the defatted alcoholic or aqueous-alcoholic extract can constitute in itself the active ingredient or active agent according to the invention.

According to another specific variant of implementation of the extraction method according to the invention, the defatted alcoholic or aqueous-alcoholic extract can be subjected to a step consisting of decolouration by filtration over an appropriate decolouring agent, such as charcoal, and then, after elimination of the charcoal, washing with a solution of an alcoholic or aqueous-alcoholic solvent which may be the same as that which was used for the initial extraction, or different.

According to another specific variant, it is possible to substantially completely evaporate off the extraction solvent, obtaining a dry extract which can either be used as it is as the active ingredient, or dissolved once again in a cosmetically acceptable solvent, in particular an alcohol or an aqueous-alcoholic mixture, in order to obtain another variant of the active ingredient.

According to another advantageous variant of the invention, the alcohol used for the extraction is ethanol.

In the context of the invention, the extract obtained is easy to use as a cosmetic agent and to mix with the other ingredients of a cosmetic composition to be prepared, regardless of whether it is for being incorporated into an aqueous phase or a fatty phase.

According to a third aspect, the present invention also relates to a cosmetic care process, characterized in that it comprises the topical application, to the skin of an individual who is in need of it, of a cosmetically effective amount of an extract of seeds of the *Aframomum angustifolium* or *Longoza* plant as defined above.

According to an advantageous embodiment of the invention, this cosmetic care process is used to apply the extract of seeds of the *Aframomum angustifolium* or *Longoza* plant to the areas of the skin which are in need of an anti-ageing care, in particular for combating the effects of ageing resulting from the action of actinic radiation, in particular ultraviolet rays.

More specifically, the anti-ageing activity is particularly aimed at an anti-wrinkle activity, for decreasing, eliminating or slowing down the appearance of wrinkles.

The invention also has an action which preserves or restores the structure of the skin, especially by means of an action which stimulates the synthesis of collagen, in particular of collagen VII, present at the dermal-epidermal junction, or DEJ, and/or by means of a repairing action on the oxytalan fibres and/or the elaunin fibres, an effect consisting of protection, repair or restoration of the elasticity and/or of the firmness of the skin.

In the context of any one of the aspects of the invention, said extract is present at a concentration, expressed on a dry extract basis, of between 0.001% and 5%, preferably of between 0.01% and 1%, by weight relative to the total weight of the composition.

BRIEF DESCRIPTION OF THE DRAWINGS

Other aims, characteristics and advantages of the invention will become clearly apparent to those skilled in the art from the following description given with reference to the attached drawings, in which:

FIG. 3 represents the results of measurement of the immunohistochemical evaluation of the collagen type VII found at the dermal-epidermal junction with, along the x-axis, respectively the results obtained with the "control skin"; with the skin subjected to UV radiation only (referred to as "+UV"); and with the skin having been subjected to the ultraviolet treatment in the presence of the same extract of *Longoza* according to the invention ("UV+*Longoza*"); and, along the y-axis, the sore obtained according to a scale ranging from 0 to 3.5, demonstrating a significant repair effect with respect to collagen VII by means of the extract of *Longoza* of the invention, compared with the skin experimentally aged by subjecting it to ultraviolet radiation;

FIG. 4A is a photograph showing a section of skin at the dermal-epidermal junction, showing the intensity of the labelling for collagen VII at the dermal-epidermal junction or DEJ ("control skin"); FIG. 4B represents, under the same conditions, the skin having been subjected to the ultraviolet radiation ("skin+UVs"); FIG. 4C represents the same skin having been subjected to the ultraviolet radiation in the presence of the extract of *Longoza* seeds according to the invention ("skin+UVs+*Longoza*"), showing that, with the extract of *Longoza* according to the invention, the intensity of the labelling observed is close to that of the control without UV.

Figure 1:
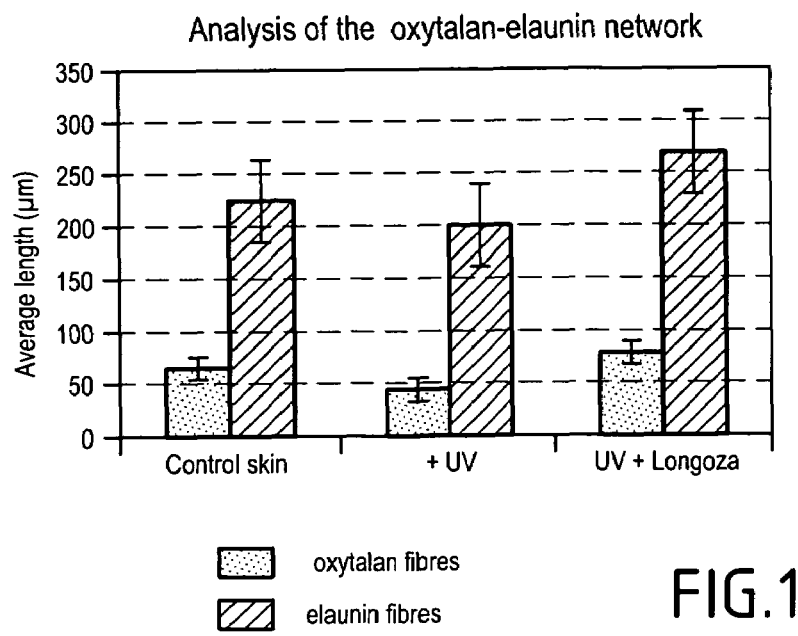
FIG. 1 represents the results of tests obtained with the extract of seeds of the *Aframomum angustifolium* or *Longoza* plant on human skin, maintained under survival conditions, artificially aged with ultraviolet radiation (results reported under the name "UV+*Longoza*"), by histological quantification of the elastic fibres by computerized image analysis through analysis of the oxytalan-elaunin network, in comparison with the same human skin forming a control skin (results reported under the name "control skin"), or the same human skin, artificially aged with UV radiation (referred to as "+UV"), reported along the x-axis; with the average length of the elastic fibres indicated along the y-axis, in micrometers on a scale ranging from 0 to 350.

In the examples hereinafter, all the percentages are given by weight, the temperature is ambient temperature, i.e. 25° C., or is given in degrees Celsius, and the pressure is atmospheric pressure, unless otherwise indicated.

EXAMPLE 1

Example of Preparation of a Defatted Alcoholic or Aqueous-Alcoholic Extract of Seeds of the *Aframomum angustifolium* or *Lonoza* Plant According to the Invention Using 100 kg of *Longoza* plant seeds from various commercial batches, available from the company SOTRAMEX, France, the following extraction procedure is carried out:

a) first of all, the commercial dried seeds are ground until, for example, an average powder size of between 0.01 mm and 1 mm is obtained;

b) next, three successive extractions of the ground seeds are carried out, each time with 500 litres (l) of an aqueous-alcoholic mixture (for example, an ethanol/water mixture in a 70/30 ratio by volume), advantageously with slight heating, for example to 50° C., with stirring, for a period of approximately 30 minutes. The preferred alcohol is ethanol for its well-known biocompatibility. It is clearly understood that the extraction could just as easily be carried out with pure alcohol.

A filtration of the extraction cake is carried out after each extraction, as is a washing procedure. The filtration is, for example, carried out through a filter having a pore diameter of 0.70 μm, the washing being carried out with 30 l of a 70/30 volume/volume aqueous-alcoholic mixture;

c) the filtrates are subsequently combined, whilst obtaining a total filtrated volume of approximately 1500 l, the solution obtained being cloudy;

d) a step consisting of elimination of the lipids, or defatting step is subsequently advantageously carried out by liquid/liquid extraction with an apolar organic solvent, for example n-heptane.

Advantageously, three extractions are carried out, each time with approximately 500 l of n-heptane with vigorous stirring.

A separation by settling out is performed so as to obtain separation of the heptane phase from the aqueous-alcoholic phase, the heptane phase being discarded.

The defatted aqueous-alcoholic phase thus obtained is virtually clear and has a volume of approximately 1500 l.

This defatted aqueous-alcoholic phase constitutes in itself, according to the embodiment currently preferred, the extract of *Longoza* or *Aframomum angustifolium* seeds according to the invention which can be used as a cosmetic agent or an active ingredient for the production of a cosmetic composition, as shown in the following examples (extract 1d). This aqueous-alcoholic solution contains 0.47% by weight of dry extract. It is understood that, by modifying the extraction parameters, such as the amount of extraction solvent used and the proportion of alcohol in the aqueous-alcoholic mixture, it is possible to obtain different contents of dry extract, for example higher contents, in particular of approximately 1% by weight; the concentration by weight of dry extract can vary within certain limits.

e) According to a variant of implementation, a step consisting of elimination of the traces of apolar organic solvent used, such as n-heptane, for example by distillation by heating the aqueous-alcoholic phase to a maximum temperature of 50° C., optionally under reduced pressure, can be carried out.

f) A dilution of the defatted alcoholic or aqueous-alcoholic solution no longer containing any apolar organic solvent can subsequently be carried out until the volume of 1500 l is again obtained, by adding alcoholic or aqueous-alcoholic solvent solution.

g) A decolouration of the defatted solution can also be carried out by treatment on charcoal, as is well known to those skilled in the art, for 1 h at ambient temperature, with stirring.

A filtration of the charcoal through a filter having a pore diameter of 0.45 μm can subsequently be carried out, followed by washing of the filtered charcoal with 3 l of alcoholic or aqueous-alcoholic solution.

The defatted and decoloured alcoholic or aqueous-alcoholic solution is clear and has a volume of approximately 1500 l.

h) A concentration of said solution can subsequently be carried out mainly by evaporation of the alcohol in order to obtain an essentially aqueous phase, in particular by heating to a moderate temperature of at most 50° C., optionally under reduced pressure. This essentially aqueous solution may also be used as it is as an active ingredient according to the solution.

i) According to yet another implementation variant, a lyophilization of said essentially aqueous solution can be carried out so as to obtain a dry extract which can also be used as it is as an active ingredient according to the invention.

j) For the incorporation of this dry extract into a cosmetic composition according to the invention, it is also possible to prepare an extemporaneous solution thereof at the time said composition is produced, in a cosmetically acceptable solvent, in particular in water, alcohol or 1,3-butylene glycol, or in a mixture of these solvents. This embodiment thus makes it possible to prepare solutions of dry extract of the *Aframomum angustifolium* or *Longoza* plant at the desired concentration.

k) Finally, a process consisting in packaging the various solutions of the extract described above, while awaiting their use for the production of the desired cosmetic compositions, can be carried out. In this context, it is preferable to perform, beforehand, a sterilizing filtration through a filter having a pore diameter of 0.22 μm, before the packaging in bottles of appropriate volumes, and then storage in a cold room, for example at 4° C.

EXAMPLE 2 ACCORDING TO THE INVENTION

Determination of the Anti-Ageing Activity of the Extract of *Longoza* (*Aframomum angustifolium*) on an Experimental Model of Human Skin Maintained Under Survival Conditions and Artificially Aged with UV Radiation In order to determine the anti-ageing activity of the extract of *Longoza* according to the invention, an experimental model of skin maintained under survival conditions and artificially aged with ultraviolet radiation ("UV") was used in order to evaluate the anti-ageing effect.

This test was evaluated by analysis of the restoration of the quality of the dermal-epidermal junction by immunohistochemical evaluation of collagen VII, and of the elastic fibres of the superficial dermis by studying the oxytalan-elaunin network, and of the middle-deep dermis by morphometric quantification by image analysis.

To do this, skin fragments were taken from women after plastic surgery, using eight different donors. These fragments were placed in inserts which were themselves placed in suspension above culture wells.

MEM culture medium, well known to those skilled in the art, supplemented with an antibiotic of gentamycin, a bovine pituitary extract, foetal calf serum and hydrocortisone, is added to the bottom of the wells. The culture medium is passed by diffusion from the base of the wells through a porous membrane which is 12 μm thick. This culture medium was removed every three days.

An experimental ageing model is realized by providing for two ultraviolet-irradiation operations, comprising a UVA component (8 J/cm$^2$) and a UVB component (2 j/cm$^2$), respectively after one day ("D1") and on the third day ("D3"), in order to cause skin alterations similar to those observed during ageing.

A solution at 5% in the culture medium of the solution of extract of *Longoza* obtained at the end of step d) in Example 1 above (extract 1d) is prepared. From the first day ("D0") to the tenth day ("D10"), this solution at 5% is applied to the surface of the skin fragments, three times a week.

In the context of this trial, a comparison is therefore made between:
a) a control skin simply placed under survival conditions;
b) a skin maintained under survival conditions, experimentally aged with UVA and B radiation (reference control skin);
c) a skin maintained under survival conditions, artificially aged with ultraviolet A/B radiation, with application of the extract of *Longoza* as indicated above.

Some skin cultures are stopped at the fourth day ("D4") for the immunohistochemical analysis of collagen VI and others are stopped on the tenth day ("D10"), for the morphometric analysis of the elastic fibres. The results obtained are as follows:

1) Histological Quantification of Elastic Fibres

The elastic fibres are visualized by (+) catechin staining and morphometrically quantified by computerized image analysis provided by a computer-assisted Leitz XC-75CE camera, the computer being equipped with software provided by the camera production.

The average length (μm) of the oxytalan and elaunin fibres of the superficial dermis is evaluated, as is their average surface area ($\mu m^2$).

In the context of the results produced by the inventors, it was possible to demonstrate, with the skin ageing model used, a statistically significant decrease in the average length of the oxytalan fibres (42.7 μm) and in the average surface area of the oxytalan and elaunin fibres of the dermis (2339 $\mu m^2$) compared with the control skin (length 64 μm and surface area 2808.9 $\mu m^2$), constituting a statistically significant value with a deviation $p<0.05$.

Figure 2A:
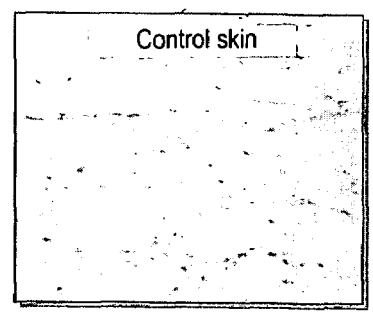
FIG. 2A shows a photograph of the control skin, taken on an electron microscope with a 400-times magnification.
Figure 2B:
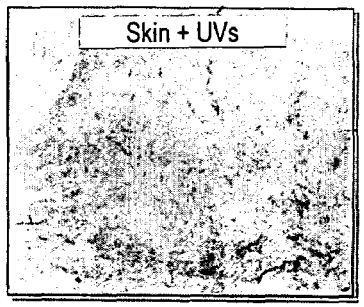
FIG. 2B shows a photograph taken, under identical conditions, of the skin having been subjected to artificial ageing with UV radiation.
Figure 2C:
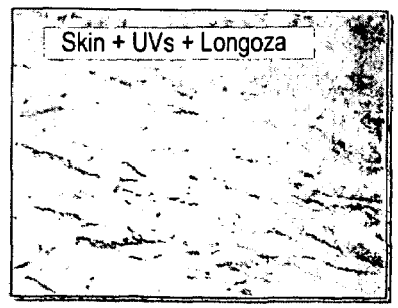
FIG. 2C shows the results obtained by combining UV-ageing in the presence of an alcoholic or aqueous-alcoholic extract of *Longoza* seeds according to the invention, prepared according to Example 1 hereinafter, showing, in the context of the invention, a restoration of the oxytalan-elaunin network and of the mature elastic fibres.

The results are reported in FIG. 1 attached to the annex and the photographs taken with the Leitz electron microscope equipped with the Leitz XC-75CE camera are the subject of FIGS. 2A (control skin), 2B (skin+UV) and 2C (skin+UV+*Longoza*).

It will be observed that the repair effect in terms of the oxytalan and elaunin fibres is significant with the extract of *Longoza* according to the invention as obtained in Example 1, in the form of a defatted alcoholic or aqueous-alcoholic extract.

Specifically, the average length of the oxytalan fibres of the skin treated with the extract of *Longoza* according to the invention is 75 μm ($p<0.05$). The average length of the elaunin fibres is increased to 267.4 μm compared with the experimentally aged skin, the length of which is reduced to 200 μm. Similarly, the average surface area of the elaunin fibres is significantly increased to 3397.2 $\mu m^2$ with a deviation $p<0.05$.

Thus, the repair effect in terms of the mature elastic fibres of the middle and deep dermis is itself also significant compared with the control+ultraviolet (+7.7% for the middle dermis and +8.4% for the deep dermis).

All these results are clearly visible in FIG. 1 attached to the annex.

2) Immunohistochemical Analysis of Collagen Type VII

Using the skin fragments taken from women after plastic surgery as indicated above, and frozen, it is possible to detect, by immunohistochemistry, the collagen type VII located at the level of the basal membrane.

The immunodetection is carried out by means of a three-layer indirect immunoperoxidase technique using a commercially available kit called ABC peroxidase, available from Vector Laboratories, USA, and visualized with a visualizing agent such as DAB (diaminobenzidine).

The evaluation is carried out by means of a semi-quantitative score ranging from 0 to 3, specifying the intensity of the labelling and the topography thereof, i.e. the more or less substantial extension at the dermal-epidermal junction.

The experimental model of ultraviolet ageing of the skin made it possible to alter the collagen VII at the dermal-epidermal junction (DEJ).

A score of 1.67 was in fact obtained compared with 2.4 for the control skin.

This difference is statistically significant with a deviation $p<0.05$.

A significant repair effect is observed in terms of collagen VII when the extract of *Longoza* according to the invention is used, compared with the skin experimentally aged with ultraviolet radiation under the conditions, with a deviation $p<0.05$.

The results of this immunohistochemical evaluation of collagen type VII, which were obtained, are reported in FIG. 3 attached in the annex.

Furthermore, FIG. 3A presents a photograph, taken under an electron microscope, of a section of control skin, FIG. 3B presents one and the same photograph for skin artificially aged with ultraviolet radiation, and FIG. 3C presents a photograph taken under the same conditions for the skin artificially aged with ultraviolet radiation and with treatment of the skin with the extract of *Longoza* according to the invention.

In the presence of UV, a decrease in intensity of the collagen VII labelling is observed at the DEJ.

On the other hand, when the skin is treated with the extract of *Longoza* according to the invention, as indicated above, a labelling intensity similar to that of the control without UV is observed, showing the effectiveness of protection given by the extract of *Longoza* according to the invention.

In conclusion to the above, by virtue of the experimental ageing model used, on human skin maintained under survival conditions, it was possible to demonstrate the significant repair effect of the extract of *Longoza* according to the invention on the oxytalan and elaunin fibres of the superficial dermis, on the elastic network of the middle and deep dermis and on collagen VII in the dermal-epidermal junction.

Thus, the invention can be used as a cosmetic agent for the preparation of the cosmetic composition for topical use with a view to preserving structural proteins such as collagen or elastin, and also for reinforcing the dermal-epidermal junction.

Various examples of formulation of a cosmetic composition are given hereinafter by way of illustration, and can therefore in no way limit the scope of the invention.

In all the examples of the description, all the percentages are given by weight, unless otherwise indicated.

EXAMPLE 3 ACCORDING TO THE INVENTION

| Cosmetic gel for improving the firmness of the face | |
|---|---|
| defatted alcoholic or aqueous-alcoholic extract of *Longoza* obtained in Example 1, d) | 2% |
| glycol | 3% |
| commercially available AMPS polymer (trade name Sepigel 305 ®) | 3% |

-continued

| Cosmetic gel for improving the firmness of the face | |
|---|---|
| hydrogenated castor oil (Cremophor CO-60 ®) | 2% |
| polyethylene glycol | 1.5% |
| preserving agent | 0.5% |
| fragrance concentrate | 0.3% |
| UV-screening agent (benzophenone-4) | 1% |
| water, qs 100% | |

This gel can be applied once a day for several weeks to the face in order to achieve an improvement in the firmness of the facial skin, and in particular to the areas comprising wrinkles, thus observing, at the end of this treatment, a restoration of the suppleness with a clear rejuvenating effect on the skin and a clear effect of reduction or disappearance of these wrinkles.

EXAMPLE 4 ACCORDING TO THE INVENTION

| Anti-wrinkle day cream in the form of an emulsion | |
|---|---|
| defatted alcoholic or aqueous-alcoholic extract of *Longoza* obtained in Example 1, d) | 2% |
| steareth-21 (Brij 721) | 2.5% |
| glyceryl stearate (Tegrin) | 1.1% |
| stearyl alcohol | 5% |
| glycerol tricaprate/caprylate | 12.5% |
| butylene glycol | 3% |
| glycerol | 2% |
| preserving agent | 0.5% |
| fragrance concentrate | 0.5% |
| UV-screening agent (octyl methoxycinnamate) | 7.5% |
| water, qs 100% | |

EXAMPLE 5 ACCORDING TO THE INVENTION

| Anti-wrinkle tonic lotion | |
|---|---|
| defatted alcoholic or aqueous-alcoholic extract of *Longoza* obtained in Example 1, d) | 2% |
| butylene glycol | 3% |
| EDTA | 0.1% |
| solubilizing agent | 1% |
| fragrance concentrate | 0.3% |
| ethanol | 5% |
| UV-screening agent (benzophenone-4) | 0.13% |
| water, qs 100% | |

EXAMPLE 6 ACCORDING TO THE INVENTION

| Facial make-up powder for protection against ultraviolet radiation | |
|---|---|
| defatted alcoholic or aqueous-alcoholic extract of *Longoza* obtained in Example 1, d) | 0.25% |
| talc | 17% |
| mica | 20% |

-continued

| Facial make-up powder for protection against ultraviolet radiation | |
|---|---|
| sericite | 20% |
| pigments | 8% |
| organic powder (nylon) | 20% |
| silica | 8.75% |
| silicone or mineral oil | 3% |
| UV-screening agent (octyl methoxycinnamate) | 3% |

EXAMPLE 7 ACCORDING TO THE INVENTION

| Anti-wrinkle treating foundation | |
|---|---|
| defatted alcoholic or aqueous-alcoholic extract of *Longoza* obtained in Example 1, d) | 2% |
| polyglyceryl-4 isostearate and cetyl dimethicone copolyol and hexyl laurate | 5.1% |
| cyclopentasiloxane and cyclohexasiloxane | 5.0% |
| cetyl dimethicone | 1.0% |
| caprylic/capric triglycerides | 2.2% |
| octyl stearate | 1.4% |
| mineral oil | 3.5% |
| hydrogenated castor oil | 1.2% |
| beeswax | 0.8% |
| poly(methyl methacrylate) | 1.1% |
| iron oxides | 0.45% |
| titanium dioxides | 5.2% |
| NaCl | 0.6% |
| fragrance concentrate | 0.1% |
| UV-screening agent (octyl cinnamate) | 3% |
| water, qs 100% | |

The invention claimed is:

1. A method of cosmetic care, comprising:
contacting the skin of an individual in need thereof with a cosmetic composition comprising an extract from the seeds of the plant *Aframomum angustifolium* wherein the extract is present at a concentration of about 0.001% to about 5% by weight of the total weight of the composition wherein said composition is applied to the areas of the skin in need of anti-ageing care.

2. The method of claim 1, wherein the extract is present at a concentration of about 0.01% to about 1% by weight of the total weight of the composition.

3. The method of claim 1, wherein said composition is applied to the areas of the skin in need of an anti-ageing care selected from the group consisting of an anti-wrinkle activity for decreasing, eliminating or slowing down the appearance of wrinkles, a care for preserving the structure of the skin, a care for restoring the structure of the skin, a care for repairing the oxytalan fibres and/or the elaunin fibres, a care for repairing skin elasticity, a care for restoration of skin elasticity, and a care for firming the skin.

4. The method of claim 1, wherein said extract from the seeds of the plant *Aframomum angustifolium* is prepared by at least one step of solvent extraction of the ground seeds with a cosmetically acceptable extraction solvent selected from an alcoholic solvent and an aqueous-alcoholic solvent.

5. The method of claim 4, wherein said extract is defatted by elimination of the lipids by performing at least one additional extraction step with an apolar organic solvent to obtain a defatted alcoholic or aqueous-alcoholic extract.

6. The method of claim 5, wherein said apolar organic solvent is selected from hexane and n-heptane.

7. The method of claim 5, wherein said defatted extract is subjected to further steps comprising:
   decoloring by filtration a decoloring agent; and
   washing with a solution of an alcoholic or aqueous-alcoholic solvent after elimination of the decoloring agent.

8. The method of claim 5, wherein said solvent is substantially completely evaporated off, thereby obtaining a dry extract.

9. The method of claim 8, further comprising dissolving said dry extract in a cosmetically acceptable solvent.

10. The method of claim 8, further comprising dissolving said dry extract in a cosmetically acceptable solvent selected from an alcohol and an aqueous-alcoholic mixture.

11. The method of claim 4, wherein the alcohol of at least one of said alcoholic solvent and of said aqueous-alcoholic solvent is selected from a monoalcohol and a polyol containing from 1 to 4 carbon atoms.

12. The method of claim 11 wherein said alcohol is selected from the group consisting of methanol, ethanol, n-propanol, isopropanol, ethylene glycol, polypropylene glycol and butylene glycol.

13. The method of claim 12, wherein said alcohol is ethanol.

* * * * *